United States Patent [19]

Yu

[11] Patent Number: 4,868,323

[45] Date of Patent: Sep. 19, 1989

[54] PREPARATION OF ISONITRILES

[75] Inventor: Lin-Chen Yu, Allison Park, Pa.

[73] Assignee: Mine Safety Appliances Company, Pittsburgh, Pa.

[21] Appl. No.: 136,343

[22] Filed: Dec. 22, 1987

[51] Int. Cl.$^4$ .................................. C07C 121/453
[52] U.S. Cl. ............................................ 558/302
[58] Field of Search ................................ 558/302

[56] References Cited

U.S. PATENT DOCUMENTS 3,636,036  1/1972  Ugi .................................. 558/302
4,186,264  1/1980  Penrose et al. .................... 548/161

Primary Examiner—Mary C. Lee
Assistant Examiner—J. Richter

[57] ABSTRACT

Phenyl isonitriles are prepared by reaction of substantially equimolar amounts on N-arylformimidates and a lithium dialkylamide.

3 Claims, No Drawings

PREPARATION OF ISONITRILES

FIELD OF THE INVENTION

The invention relates to a new and improved method of preparing isonitriles and more particularly to the preparation of phenyl isonitriles by reaction of lithium dialkylamide and N-arylformimidates.

BACKGROUND OF THE INVENTION

Isonitriles are the only class of stable organic compounds containing formally divalent carbon. The terminal carbon adjacent to the nitrogen behaves as an electrophile and/or a nucleophile during reactions. The unique reactivity of this divalent carbon accounts for the wide variety of reactions, particularly multicomponent reactions, and makes them useful intermediates for the synthesis of a wide variety of compounds. Reactions involving phosgene methods are now most widely used for the preparation of isonitriles. Due to the high toxicity of phosgene, an alternate, convenient, and high yield method would be very desirable. Powers, J. C.; Seidner, R.; Parsons, T. G.; Berwin, H. J. J. Org. Chem. 1966, 31, 2623. report the reaction of formimidates with sodium hydride gave amidine as the only isolable product. Koga, N.; Koga, G.; Anselme, J.-P. Tetrahedron Lett., 1970, 3309. report attempts to prepare isonitriles by the α-elimination of the elements ROH from formimidate derivatives by reaction with alkyllithium and triphenylmethyllithium. Reported isonitrile yields were only from trace amounts to 20% and the authors noted that "Exploratory attempts to make this approach a useful isonitrile synthesis were not rewarding."

Pornet, J.; Miginiac, M. L. Tetrahedron Lett., 1971, 967. report yields of 45% and 60% from reaction of ethyl N-(4-methoxyphenyl)formimidate and ethyl N-phenylformimidate with the aminomagnesium reagent [(CH$_3$)$_2$CH]$_2$ N-MgBr.

SUMMARY OF THE INVENTION

It is an object of this invention to provide a method of preparing isonitriles in good yields from formimidates by reaction with a low nucleophilic strong base.

In accordance with the invention an N-aryl formimidate of the general formula

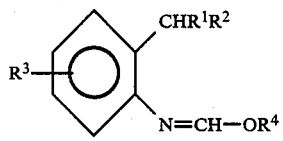

where R$^1$ and R$^2$ are independently H or an alkyl radical, preferably a lower alkyl radical, R$^3$ is one or more substituents on the aryl ring carbons being H, alkyl, alkoxy, halogen, aryl or aryloxy, and R$_4$ is an alkyl radical, preferably methyl, ethyl or isopropyl; is reacted with an equimolar amount of lithium dialkylamide of the formula LiNR$^5$R$^6$ in which R$^5$ and R$^6$ are independently a lower alkyl radical at least one of R$^5$ or R$^6$ having at least 3 carbon atoms, or a branched cycloalkyl radical, to yield phenylisonitriles of the formula

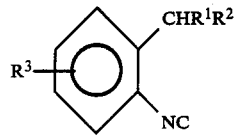

As used herein, "lower alkyl" denotes a straight chain or branched-chain saturated hydrocarbon group containing 1 to 8 carbon atoms, and "branched cycloalkyl" denotes an α-alkylsubstituted or an α,α$^1$-dialkylsubstituted cycloalkyl radical, in which the cycloalkyl radical contains from 3 to 6 carbons.

The copending application Ser. No. 06/768,461, of common ownership with this application, discloses the preparation of indoles by reaction of formimidates with alkali metal dialkylamides. The reaction requires 2 moles of alkali metal dialkylamide for each mol of fomimidate. According to the instant invention, the reaction is directed to give high yields of isonitriles by using only 1 mol of a lithium dialkylamide for each mol of formimidate. Other alkali metal dialkylamides are not suitable for use in the reaction to form isonitriles. For example, when 1 mol of potassium dialkylamide was reacted with 1 mol of formimidate, the yield of indole was 39% and no isonitrile was formed.

DESCRIPTION OF THE PREFERRED EMBODIMENTS

The reactant N-arylformimidates used in the method of the invention are known materials that can be prepared in good yield by the known reaction of anilines and triethyl orthoformate in the presence of a catalytic amount of an acid. For example, ethyl N-(2-isopropylphenyl)formimidate was prepared by refluxing for three hours a solution of 2-isopropylaniline (135.2 g.) in triethyl orthoformate (592.8 g.) in the presence of 85% phosphoric acid (0.14 g.). Ethanol and excess of triethyl orthoformate were distilled out. Distillation of the residue gave 187.6 g. of ethyl N-(2-isopropylphenyl)formimidate in 98% yield.

The N-arylformimidate and lithium dialkylamide are contacted at temperatures between about −78° C. and 25° C. in an inert solvent, such as for example tetrahydrofuran. In most instances it is preferred to use low temperatures but the most advantageous temperature and reaction time will vary depending on the specific reactants used. Excessive reaction time or too high temperatures are evidenced by a reduced yield of isonitrile and the formation of formamidines.

The reactants are used in approximately equimolar proportions. Excess amounts of lithium dialkylamide are to be avoided as the yield may be reduced by metallation of the benzylic position resulting in the formation of indoles through cyclization. It is convenient, as in the following examples, to form the lithium dialkylamide in situ in the reaction solvent.

EXAMPLE I

A single-neck, 250 ml. round bottom flask was equipped with a three-way stopcock which was connected to a vacuum-nitrogen manifold system. To this flask was successively charged dry tetrahydrofuran (120 ml), diisopropylamine (7.7 ml.), and 21.8 ml. of n-butyllithium (2.52 M in hexane) under nitrogen. The solution was stirred at 25° C. for 0.5 hours to form lithium diisopropylamide and was then cooled to −78°

C. by immersing the flask into an acetone-dry ice bath. Ethyl N-(2-isopropylphenyl)formimidate (10.00 g.) was added slowly over a period of 9 minutes. The yellowish solution was stirred at −78° C. for 45 minutes and was quenched with 10 ml. of saturated, aqueous ammonium chloride solution. The mixture was partitioned between diethyl ether (30 ml.) and water (30 ml.). Aqueous layer was separated and extracted with diethyl ether (3×30 ml.). All organic layers were combined, washed with water (20 ml.) and then brine (20 ml.), dried (anhydrous magnesium sulfate), and concentrated. Distillation of the crude product gave 7.20 g. (95% yield) of 2-isopropylphenyl isonitrile.

EXAMPLE II

The general procedure of example I was repeated using the reactant formimidate identified below resulting in the indicated yield of the indicated isonitrile:

| formimidate | isonitrile | % yield |
| --- | --- | --- |
| ethyl N—(2-ethylphenyl)formimidate | 2-ethylphenyl isonitrile | 92 |
| methyl N—(2-ethylphenyl)formimidate | 2-ethylphenyl isonitrile | 83 |
| ethyl N—(2-isopropylphenyl)-formimidate | 2-isonpropylphenyl isonitrile | 95 |
| ethyl N—(2,6-dimethylphenyl)-formimidate | 2,6-dimethylphenyl isonitrile | 85 |
| methyl N—(2,6-diethylphenyl) formimidate | 2,6-diethylphenyl isonitrile | 87 |
| ethyl N—(2-methyl-6-ethylphenyl)-formimidate | 2-methyl-6-ethylphenyl isonitrile | 83 |

I claim:

1. A method of preparing phenyl isonitriles comprising the step of contacting and reacting substantially equimolar amounts of a formimidate of the formula

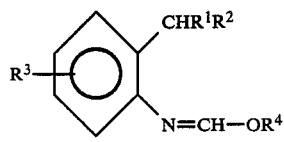

where $R_1$ and $R^2$ are independently H or an alkyl radical, $R^3$ is independently one or more of H, alkyl, alkoxy, halogen, aryl or aryloxy, and $R^4$ is a lower alkyl radical, with a lithium dialkylamide of the formula $$LiNR^5R^6,$$

where $R^5$ and $R^6$ are independently an alkyl radical, at least one of $R^5$ or $R^6$ having at least 3 carbon atoms, or a branched cycloalkyl radical, and recovering the phenyl isonitrile formed thereby.

2. A method in accordance with claim 1 in which $R^4$ is methyl, ethyl or isopropyl.

3. A method according to claim 1 in which $R^5$ and $R^6$ are isopropyl.

* * * * *